US008592147B2

(12) United States Patent
Chang et al.

(10) Patent No.: US 8,592,147 B2
(45) Date of Patent: Nov. 26, 2013

(54) HIGH-CONTENT SCREENING FOR DRUGS AGAINST CANCER AND AGE-RELATED DISEASES

(75) Inventors: Bey-Dih Chang, Rensselaer, NY (US); Igor B. Roninson, Loudonville, NY (US)

(73) Assignee: Senex Biotechnology, Columbia, SC (US)

( * ) Notice: Subject to any disclaimer, the term of this patent is extended or adjusted under 35 U.S.C. 154(b) by 1662 days.

(21) Appl. No.: 11/331,429

(22) Filed: Jan. 12, 2006

(65) Prior Publication Data

US 2006/0154287 A1 Jul. 13, 2006

Related U.S. Application Data

(60) Provisional application No. 60/643,561, filed on Jan. 13, 2005.

(51) Int. Cl.
*C12Q 1/68* (2006.01)

(52) U.S. Cl.
USPC ............................................ 435/6.1; 435/6.13

(58) Field of Classification Search
USPC ..................................... 435/6, 6.13
See application file for complete search history.

(56) References Cited

U.S. PATENT DOCUMENTS

| 6,706,491 B1 | 3/2004 | Chang et al. | |
|---|---|---|---|
| 2003/0064426 A1* | 4/2003 | Poole et al. | 435/8 |
| 2003/0157704 A1 | 8/2003 | Roninson et al. | |

FOREIGN PATENT DOCUMENTS

| WO | WO9950280 | 10/1999 |
|---|---|---|
| WO | WO2004078985 | 9/2004 |

OTHER PUBLICATIONS

Schmid and Sakamoto. Current Protocols in Cytometery unit 7.16:7.16.1-7.16.10, 2001.*
Scarff et al. Genesis 36:149-157, 2003.*
Hayflick et al., "The Serial Cultivation of Human Diploid Cell Strains", Exp. Cell Res., 25:585-621 (1961).
Mathon et al., "Cell Senescence and Cancer", Nat. Rev. Cancer, 1:203-213 (2001).
Vaziri et al., "ATM-Dependent Telomere Loss in Aging Human Diploid Fibroblasts and DNA Damage Lead to the Post-Translational Activation of p53 Protein Involving Poly(ADP-Ribose) Polymerase", EMBO J., 16(19):6018-6033 (1997).
Di Leonardo et al., "DNA Damage Triggers a Prolonged p53-Dependent $G_1$ Arrest and Long-Term Induction of Cip1 in Normal Human Fibroblasts", Genes Dev., 8:2540-2551 (1994).
Serrano et al., "Oncogenic ras Provokes Premature Cell Senescence Associated with Accumulation of p53 and $p16^{INK4a}$", Cell, 88:593-602 (1997).
Campisi, Judith, "Cellular Senescence as a Tumor-Suppressor Mechanism", Trends Cell. Biol., 11(11):S27-S31 (2001).
Campisi, J., "From Cells to Organisms: Can We Learn About Aging From Cells in Culture?", Exp. Gerontology., 36:607-618 (2001).
Krtolica et al., "Senescent Fibroblasts Promote Epithelial Cell Growth and Tumorigenesis: A Link Between Cancer and Aging", Proc. Natl. Acad. Sci. USA, 98(21):12072-12077 (2001).
Roninson, Igor B., "Tumor Cell Senescence in Cancer Treatment", Cancer Res., 63:2705-2715 (2003).
Mainprize et al., "Cip/Kip Cell-Cycle Inhibitors: A Neuro-Oncological Perspective", Journal of Neuro-Oncology, 51:205-218 (2001).
Kopnin, B.P., "Targets of Oncogenes and Tumor Suppressors: Key for Understanding Basic Mechanisms of Carcinogenesis", Biochem. (Moscow), 65(1):2-27 (2000).
Deuschle et al., "Tetracycline-Reversible Silencing of Eukaryotic Promoters", Mol. and Cell. Biol., 15(4):1907-1914 (1995).
Rossi et al., "Recent Advances in Inducible Gene Expression Systems", Curr. Opin. Biotechnology, 9:451-456 (1998).
Chang et al., "Role of p53 and $p21^{waf1/cip1}$ in Senescence-Like Terminal Proliferation Arrest Induced in Human Tumor Cells by Chemotherapeutic Drugs", Oncogene, 18:4808-4818 (1999).
Chang et al; "Effects of P21WAF1/CIP1/SDI1 on Cellular Gene Expression: Implications for Carcinogenesis, Senescence, and Age-Related Diseases"; Proceedings of the Natl. Acad. of Sci. of USA; 97(8):4291-4296 (2000).

* cited by examiner

*Primary Examiner* — Marcia S Noble
(74) *Attorney, Agent, or Firm* — Wayne A. Keown

(57) ABSTRACT

The invention relates to methods for high-throughput screening for compounds that modulate cell growth or promoter activity. The invention provides the use of cell lines with properly regulated promoter-reporter expression, suitable for high-throughput screening. More particularly, the invention relates to such screening to identify compounds that affect cell growth and/or that modulate the effect of cell cycle arrest on the function of a promoter that is responsive to cell cycle inhibition.

10 Claims, 3 Drawing Sheets

HIGH-CONTENT SCREENING FOR DRUGS AGAINST CANCER AND AGE-RELATED DISEASES

RELATED APPLICATIONS

This application claims the benefit of U.S. Provisional Patent Application Ser. No. 60/643,561 filed on Jan. 13, 2005, the contents of which is incorporated herein by reference in its entirety.

FIELD OF THE INVENTION

This invention is related to the discovery of drugs against cancer and age-related diseases.

SUMMARY OF THE RELATED ART

Many cells in the human body lose their ability to proliferate. One of the principal physiological programs of terminal growth arrest is known as cell senescence. Hayflick and Moorhead, Exp. Cell Res., 37:585-621, (1961) originally described senescence ("growing old") in normal human cells explanted in culture; such cells undergo a finite number of divisions before permanent growth arrest. Mathon and Lloyd, Nat. Rev. Cancer, 1:203-213, (2001) teach that this gradual process of "replicative senescence" in human cells results primarily from the shortening and other structural changes of telomeres at the ends of the chromosomes. Vaziri et al., EMBO J., 16:6018-6033, (1997) teach that telomeric changes in cells undergoing replicative senescence show similarities with DNA damage or may even directly involve such damage. Di Leonardo et al., Genes Dev., 8:2540-2551, (1994) showed that DNA damage was also found to induce rapid cell growth arrest, which was characterized as phenotypically indistinguishable from replicative senescence. Serrano et al., Cell, 88:593-602, (1997) teach that this "accelerated senescence," which does not involve telomere shortening, is also triggered in normal cells by the expression of mutant Ras or Raf and as taught in Campisi, Trends Cell Biol. 11:S27-S31, (2001), by some other forms of supraphysiological mitogenic signaling.

Both replicative and accelerated senescence are believed to be essential anticarcinogenic programs in normal cells. Replicative senescence imposes a limit on the total number of divisions a cell can undergo, and it should be expected, therefore, to interfere with tumor growth. The tumor-suppressive function is likely to be central to the program of accelerated senescence, which prevents the outgrowth of cells that have experienced oncogenic mutations (such as RAS or RAF mutations) or that underwent genome-destabilizing DNA damage. Accelerated senescence arrests proliferation in response to damage or stimuli that put cells at risk for neoplastic transformation. However, senescent cells also secrete growth factors as well as extracellular matrix components, matrix-degrading enzymes, and inflammatory cytokines that can disrupt tissue integrity and/or stimulate nearby cells to proliferate (Campisi, Exp. Gerontol 36, 607-618, 2001). As a result, senescent fibroblasts admixed with transformed epithelial cells stimulate the growth of the latter in culture as well as in tumor models (Krtolica A., Parrinello S., Lockett S., Desprez P. Y., & Campisi J. (2001). Proc. Natl. Acad. Sci. U.S.A 98, 12072-12077). Thus, senescent stromal cells create a pro-cancer environment that may synergize with oncogenic mutations to drive the rise in cancer incidence with age.

Growth arrest of normal senescent cells is executed through a chain of events that includes the activation of a regulatory protein p53, which induces transcription of a cyclin-dependent kinase (CDK) inhibitor p21 (a.k.a Waf1, Cip1, Sdi1). p21 induction leads to cell cycle arrest at the onset of senescence. Subsequently, the expression of p53 and p21 decreases, but another CDK inhibitor, p16 (a.k.a. Ink4A) becomes stably upregulated, and it is believed to be responsible for maintaining the growth-arrested state of senescent cells. Neoplastic transformation almost inevitably involves one or more events that inhibit the program of senescence, such as inactivation of tumor suppressors p53 and p16 (although p21 is very rarely inactivated in tumor cells), and tumor cells were believed until recently to have lost the ability to senesce. It has now become apparent, however, that tumor cells can be induced to undergo senescence by genetic manipulations or by treatment with chemotherapeutic drugs, radiation, or differentiating agents. (Roninson I. B. (2003). Cancer Res. 63, 2705-2715).

Senescence is associated with the induction of multiple genes, which account for different aspects of the senescent phenotype. While some of these genes act as tumor suppressors, a subset of genes induced in senescent cells encode secreted factors with tumor-promoting activities. These activities are mediated in part through the induction of p21. p21 induction leads to transcriptional activation of many genes with potential pathogenic effects. These include secreted tumor-promoting factors, as well as several genes implicated in age-related diseases, such as Alzheimer's disease, atherosclerosis or arthritis. The ability to activate such genes is shared by p21 with other CDK inhibitors, such as p16 or p27 (Roninson, 2003). CDK inhibitors are induced not only in senescent cells but also in most other forms of cell cycle arrest, and therefore many types of cell cycle arrest lead to the expression of genes that promote the development of human diseases.

Thus there remains a need for reagents and methods for identifying compounds that inhibit changes in gene expression associated with senescence and other forms of cell cycle arrest, with a goal of developing drugs that will inhibit the undesirable side effects of cell growth inhibition. A general method for identifying compounds that have such an activity in cells expressing CDK inhibitors has been developed by instant inventors (U.S. Pat. No. 6,706,491). There remains, however, a need for more sensitive assays for high throughput screening.

Many anticancer drugs have been discovered after screening multiple compounds for the ability to inhibit cell growth. Such screening assays are typically conducted using actively proliferating cell cultures. Essentially all of the chemotherapeutic drugs that have proved their efficacy in cancer treatment stop the growth or kill the proliferating cells, which is essential for their activity, since tumor cells are characterized by the ability to undergo uncontrolled proliferation. Such successful drugs, however, show much lower activity in cells that do not proliferate, and the lack of toxicity to non-proliferating, growth-arrested cells (such as most of the normal cells in the body) is essential for being able to administer such drugs safely to a patient. There remains a need for methods for identifying growth-inhibitory compounds that decrease the number of proliferating cells to a greater degree than they decrease the number of growth-arrested cells.

Because of the high cost of conducting separate screening for compounds that either modulate the side effects of cell cycle arrest or affect the growth or survival of proliferating or growth-arrested cells, there also remains a need for a high-content screening system for simultaneous identification of compounds with any of the above properties.

BRIEF SUMMARY OF THE INVENTION

The invention provides novel techniques for using a stably transfected cell line showing proper promoter regulation for rapidly and efficiently identifying small molecule drug lead compounds that affect cell growth or survival and/or that modulate the effect of cell cycle arrest on the function of a promoter that is responsive to cell cycle inhibition.

In a first aspect, the invention provides a method for identifying a bioactive substance that has a differential effect on the growth or survival of proliferating and growth-arrested cells. In the method according to this aspect of the invention, cells comprising an inducible promoter operatively associated with a gene that encodes a protein that directly or indirectly inhibits cell cycle progression are provided and contacted with a test bioactive substance under conditions in which the inducible promoter is activated or not activated. The total cell number or the total cell mass are then assayed. The test bioactive substance is identified as a substance that has a differential effect on the growth or survival of proliferating and growth-arrested cells if either the total cell number or the total cell mass under conditions in which the inducible promoter is activated or not activated is different in the presence of the bioactive substance compared to the total cell number or total cell mass in the absence of the bioactive substance.

In a second aspect, the invention provides a method for identifying a bioactive substance that modulates the effect of cell cycle inhibition on the function of a promoter that is responsive to cell cycle inhibition. In the method according to this aspect of the invention, cells comprising a first inducible promoter operatively associated with a gene that encodes a protein that directly or indirectly inhibits cell cycle progression and a second promoter responsive to cell cycle inhibition and operatively associated with a gene encoding a detectable protein are provided and contacted with a test bioactive substance under conditions in which the first promoter is activated or not activated. The total cell number and the level of detectable protein are then assayed and the ratio of detectable protein to the total cell number is determined. The test bioactive substance is identified as a substance that modulates the effect of cell cycle arrest on transcription if the ratio of detectable protein to the total cell number under conditions in which the first promoter is activated or not activated is different in the presence of the bioactive substance compared to the ratio in the absence of the bioactive substance.

In a third aspect, the invention provides a method for identifying a bioactive substance that has a effect either on cell growth or a promoter responsive to cell cycle inhibition. In the method according to this aspect of the invention, cells comprising a first inducible promoter operatively associated with a gene that encodes a protein that directly or indirectly inhibits cell cycle progression and a second promoter responsive to cell cycle inhibition and operatively associated with a gene encoding a detectable protein are provided and contacted with test bioactive substance under conditions in which the first promoter is activated or not activated. The total cell number and the level of detectable protein are then assayed and the ratio of detectable protein to the total cell number is determined. The test bioactive substance is identified as a substance that has an effect on cell growth if the total cell number under conditions in which the first promoter is activated or not activated is different in the presence of the bioactive substance than in the absence of the bioactive substance. The test bioactive substance is identified as a substance that has an effect on a promoter responsive to cell cycle inhibition if the ratio of detectable protein to the total cell number under conditions in which the first promoter is activated or not activated is different in the presence of the bioactive substance compared to the ratio in the absence of the bioactive substance.

DETAILED DESCRIPTION OF THE INVENTION

Figure 1:
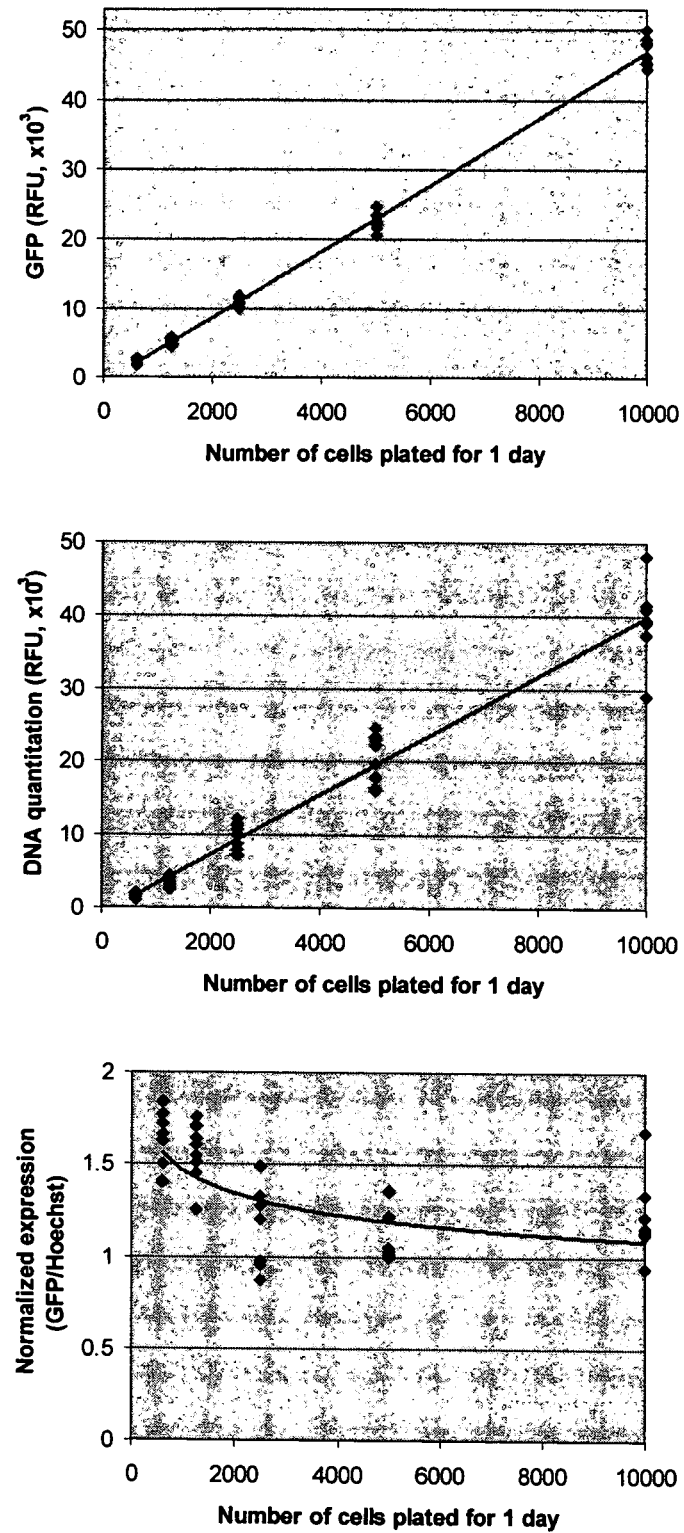
FIG. 1 shows the result of a preliminary assay carried out one day after plating cells stably transduced with CMV promoter-GFP construct in the absence of IPTG, to determine the effect of the number of cells plated in each well on GFP fluorescence (top panel), Hoechst 33342 fluorescence (middle panel), and the normalized CMV promoter function, expressed as the ratio of GFP to Hoechst fluorescence (bottom panel).

The invention relates to methods for high-throughput screening for compounds that affect cell growth or modulate promoter activity. More particularly, the invention relates to such screening to identify compounds that affect cell growth and/or that modulate the effect of cell cycle arrest on the function of a promoter that is responsive to cell cycle inhibition. The patents and publications cited herein reflect the level of knowledge in the art and are hereby incorporated by reference in their entirety. Any conflict between the teachings of these patents and publications and this specification shall be resolved in favor of the latter.

In a first aspect, the invention provides a method for identifying a bioactive substance that differentially affects the growth and survival of proliferating relative to growth-arrested cells. In the method according to this aspect of the invention, cells comprising an inducible promoter operatively associated with a gene that encodes a protein that directly or indirectly inhibits cell cycle progression are provided and contacted with a test bioactive substance under conditions in which the inducible promoter is activated or not activated. The total cell number or the total cell mass are then assayed. The test bioactive substance is identified as a substance that differentially affects the growth and survival of proliferating relative to growth-arrested cells if the total cell number or total cell mass under conditions in which the inducible promoter is activated or not activated is different in the presence of the bioactive substance compared to the total cell number in the absence of the bioactive substance.

In this aspect of the invention, the cells, in the absence of a bioactive substance, will proliferate under conditions in which the inducible promoter is not activated. If the inducible promoter is activated, the gene in operative association therewith will be transcribed and translated. The resulting protein will directly or indirectly inhibit cell cycle progression leading to cell growth arrest. The level of cell growth and cell growth arrest can be measured and the results can be compared to cells under the same conditions but in the presence of the bioactive substance. As used herein, the phrase "directly or indirectly" means that when the gene is expressed cell cycle progression is diminished regardless of specific mechanism of action.

In a preferred embodiment, the cells comprise a recombinant expression construct encoding an inducible gene that directly or indirectly inhibits cell cycle progression. More preferably, the construct comprises a nucleotide sequence encoding the gene, preferably a human gene, under the transcriptional control of an inducible promoter. Examples of genes that inhibit cell cycle progression include, but are not limited to, those shown in FIG. 1 of Mainprize et al., Journal of Neuro-Oncology, 51:205-215 (2001) and in Table 2 of Kopnin, Biochemistry (Moscow), 65(1):2-27 (2000), which are incorporated herein by reference in their entirety.

Recombinant expression constructs can be introduced into appropriate mammalian cells as understood by those with skill in the art. Although the Examples disclose recombinant mammalian cells comprising recombinant expression constructs encoding such an inducible gene, it will be understood that these embodiments are merely a matter of experimental design choice and convenience, and that the invention fully encompasses induction of an endogenous gene that directly or indirectly inhibits cell cycle progression.

As used herein, the inducible promoter operatively associated with a gene that encodes a protein that inhibits cell cycle progression is responsive to a trans-acting factor whose effects can be modulated by an inducing agent. The inducing agent can be any factor that can be manipulated experimentally, including, but not limited to temperature or the presence or absence of an inducing or inhibiting agent. In one embodiment, cells are used in which the gene of interest is under the control of the lac operon and thus can be induced by contacting the cells with β-galactosides, such as IPTG. Typically, cells are grown in appropriate culture media as known by those skilled in the art, and gene expression is induced by adding IPTG to the culture media at an appropriate concentration. Alternatively, different inducible systems can be used including, but not limited to tTR-KRAB (as discussed in Deuschle et al., Mol. and Cellular Biol., 15:1907-1914 (1995), other tetracycline (tet)-on as well as tet-off promoter systems, FK506/Rapamycin system, Ecdysone-responsive promoters, glucocorticoid-inducible MMTV promoter, Zn-inducible Metallothionein promoter, or other inducible systems described in Rossi and Blau, Curr. Opin. Biotechnol. 9, 451-456, (1998) which is incorporated herein by reference in its entirety. Typically, the gene that inhibits cell cycle progression is induced in these cells in the presence or absence of the compound to be tested according to the methods of the invention.

As used herein, the cells can include any mammalian cell, preferably a rodent or primate cell, more preferably a mouse cell and most preferably a human cell, that can induce expression of the gene that inhibits cell cycle progression, wherein such gene is either the endogenous gene or an exogenous gene introduced by genetic engineering. A particularly preferred embodiment are fibrosarcoma cells, more preferably human fibrosarcoma cells, including but not limited to human HT1080 fibrosarcoma cell line and derivatives thereof.

The total cell count is distinguished herein from the total cell mass, albeit both measures are used interchangeably in the art to measure cell growth. The total cell count is defined herein as a value that either directly represents the number of cells or provides an indirect measure of the same number, without regard to the cell size. The total cell mass is defined herein as a value that is affected both by the cell number and the cell size. The need for distinguishing between these two parameters under the present invention follows from the fact that cell cycle arrest generally prevents cells from dividing and thereby increasing their number but does not prevent the arrested cells from increasing their size and mass. For purposes of this invention, total cell number is the most preferred method due to the increased sensitivity of the assay.

In one preferred embodiment of this aspect of the invention, the total cell number is assayed directly by cell counting. Cells can be counted by various means including, but not limited to, cell counting under microscope, using a Coulter counter or a fluorescence-activated cell sorter (FACS). In another preferred embodiment, the total cell number is measured indirectly, by determining the total DNA content. Although the amount of DNA in an individual cell can differ up to two-fold depending on the stage of the cell cycle, the presence of cells in all the phases of the cycle within a proliferating cell population assures that the differences between the average DNA content in a proliferating and a growth-arrested cell population will always be less than two-fold, wherein the average cell mass of a growth-arrested and in particular a senescent cell can exceed that of a proliferating cell to a much greater degree. The total DNA content can be determined by adding a detectable DNA binding agent to the cells and determining the total DNA content of the cells by measuring the amount of the detectable DNA binding agent bound to DNA. Preferred DNA binding agents include without limitation Hoechst 33342, Hoechst 33258, Hoechst 34580, acridine orange, ethidium bromide, propidium iodide, 7-AAD and DAPI. The DNA binding agent can be detected by fluorometry, flow cytometry and/or fluorescence microscopy. The total cell mass can be assayed, for example, by measuring the total amount of cell protein, or by cell staining with methylene blue, followed by colorimetry and/or flow cytometry, or by live-cell specific staining (e.g. tetrazolium salts) followed by colorimetry, spectrophotometry or fluorometry.

Test compound, compound and bioactive substance are used interchangeably herein to describe any natural or synthetic compounds or organic small molecule compounds.

In one embodiment of this aspect of the invention, the test compound is identified as a growth inhibitory compound with specificity for proliferating cells if the total cell number or the total cell mass decreases in the presence of the compound under conditions where the promoter is not activated compared to the total cell number or the total cell mass in the absence of the compound to a greater degree that under conditions where the promoter is activated.

Growth inhibitory compounds with specificity for proliferating cells produce a decrease in cellular proliferation as measured by the total cell number or the total cell mass. This group of compounds may be cytostatic or cytotoxic and may include potential inducers of cell death or senescence.

In a further embodiment of this aspect of the invention, the test compound is identified as a compound that is toxic to growth arrested cells if the total cell number or the total cell mass decreases in the presence of the compound under conditions where the inducible promoter is activated compared to the total cell number in the absence of the compound.

Test compounds that are found to affect cell growth will be then subjected to Combinatorial Chemistry (CC) to identify further related compounds. CC will be used via computer-aided drug design and automated organic synthesis to allow thousands of compounds (a library) of systematic variants of a parent chemical structure to be produced in parallel. Through the use of this technique, new related compounds are identified by screening combinatorial libraries of synthetic small molecule compounds, determining which compound(s) have the highest probability of providing an effective therapeutic and then optimizing the therapeutic properties of the identified small molecule compound(s) by synthesizing structurally related analogs and analyzing them for binding to the target molecule. Thus, millions of new compounds designed to target a specific cellular substrate such as receptors, enzymes, structural proteins and DNA can now be created in a relatively short time. Combinatorial libraries of small molecule compounds can be obtained, for example, from ChemBridge Corporation, San Diego, Calif.

In a second aspect, the invention provides a method for identifying a bioactive substance that modulates the effect of cell cycle inhibition on the function of a promoter that is responsive to cell cycle inhibition. In the method according to this aspect of the invention, cells comprising a first inducible promoter operatively associated with a gene that encodes a protein that directly or indirectly inhibits cell cycle progression and a second promoter responsive to cell cycle inhibition and operatively associated with a gene encoding a detectable protein are provided and contacted with a test bioactive substance under conditions in which the first promoter is activated or not activated. The total cell number and the level of detectable protein are then assayed and the ratio of detectable protein to the total cell number is determined. The test bioactive substance is identified as a substance that modulates the effect of cell cycle arrest on the promoter activity if the ratio of detectable protein to the total cell number under conditions in which the first promoter is activated or not activated is different in the presence of the bioactive substance compared to the ratio in the absence of the bioactive substance.

In this aspect of the invention, the cells, in the absence of a bioactive substance, will proliferate under conditions in which the inducible promoter is not activated. Additionally, if the second promoter is up-regulated under conditions of cell cycle inhibition, the detectable protein will be expressed only at low basal levels. If the inducible promoter is activated, the gene in operative association therewith will be transcribed and translated. The resulting protein will inhibit cell cycle progression leading to cell growth arrest, up-regulation of the second promoter and the resulting increase in the expression of the detectable protein. The total cell number and detectable protein can be measured. The ratio of total content of the detectable protein to the total cell number after cells are not treated with a test compound under conditions in which the first promoter is activated or not activated is compared to the total content of the detectable protein and the total cell number of cells treated with the test compound under conditions in which the first promoter is activated or not activated. The use of total cell number rather than total cell mass is shown herein to provide a great increase in the sensitivity of the assay. For example, in a representative assay when a measure of total cell number was used for normalization, the average ratio of detectable protein to cell number, under conditions in which the inducible promoter was activated, increased by 15-18-fold, compared to the maximal induction of only 4.5-fold for protein content normalization in the same cells (data not shown). Hence, the use of total cell number instead of total cell mass greatly increases the sensitivity of the assay and makes it much more suitable for high-throughput screening.

In this aspect of the invention, the cells comprise an expression vector encoding a reporter gene under the transcriptional control of a promoter that is responsive to cell cycle inhibition, and a further recombinant expression construct encoding the gene that inhibits cell cycle progression, wherein expression of the gene that inhibits cell cycle progression can be induced in the cell. Recombinant expression constructs can be introduced into appropriate cells as understood by those with skill in the art. Preferred host cells include mammalian cells, preferably rodent or primate cells, and more preferably mouse or human cells. A particularly preferred embodiment are fibrosarcoma cells, preferably human fibrosarcoma cells including without limitation human HT1080 fibrosarcoma cell line and derivatives thereof.

In this aspect of the invention, preferred expression vectors include, but are not limited to plasmid vectors that are introduced into a cell by DNA transfection, which can be either stable or transient, and viral vectors, which introduce their genetic information into the cell via transduction with infectious recombinant virus particles. Among viral vectors, the preferred types are retroviral or lentiviral vectors, which provide very high efficiency of stable transduction. Particularly preferred are retroviral or lentiviral vectors of the self-inactivating (SIN) type, which inactivate their intrinsic LTR promoter upon provirus integration, thereby leaving the promoters of the instant invention as the only active promoters within the integrated provirus.

As described above, the recombinant expression construct encoding a gene that inhibits cell cycle progression is under the transcriptional control of an inducible promoter, and expression of the gene from the recombinant expression construct is mediated by contacting the recombinant cell with an inducing agent. As used herein, an inducing agent acts by inducing the expression of the gene that inhibits cell cycle progression and in turn modulates transcription of the gene or by removing or inactivating an agent that inhibits transcription from such promoter.

In a preferred embodiment, the promoter, which is in operable association with the reporter gene, is down-regulated under conditions of cell cycle arrest. In other preferred embodiments, the promoter, which is in operable association with the reporter gene, is up-regulated under conditions of cell cycle arrest. In one embodiment, the reporter gene encodes a detectable protein. Preferred reporter genes comprising the recombinant expression constructs of the invention include, without limitation, firefly luciferase, Renilla luciferase, chloramphenicol acetyltransferase, beta-galactosidase, green fluorescent protein, yellow fluorescent protein, cyan fluorescent protein, fluorescent protein DsRed, alkaline phosphatase or an immunologically detectable protein or peptide. Preferably the detectable protein is a fluorescent protein, more preferably the fluorescent protein is green fluorescent protein. The product of the reporter gene that is up-regulated or down-regulated under conditions of cell cycle arrest is generally detected using art-recognized techniques, such as assaying for an enzymatic activity of the gene product, detecting expression of said product using an immunological reagent, or by detecting RNA cognate to the gene by hybridization to a complementary nucleic acid. In a preferred aspect, the reporter gene is detected by fluorometry.

In one preferred embodiment of this aspect of the invention, the total cell number is assayed by cell counting or by adding a detectable DNA binding agent to the cells and determining the total DNA content of the cells by measuring the amount of the detectable DNA binding agent bound to DNA. Cells can be counted by various means including, but not limited to, cell counting under microscope, using a Coulter counter or FACS. Preferred DNA binding agents include without limitation Hoechst 33342, Hoechst 33258, Hoechst 34580, acridine orange, ethidium bromide, propidium iodide, 7-AAD and DAPI. The DNA binding agent can be detected by fluorometry, flow cytometry and/or fluorescence microscopy. The total cell number after cells are contacted with a test compound under conditions in which the inducible promoter is activated or not activated is compared to the total cell number of cells not treated with the test compound under conditions in which the inducible promoter is activated or not activated.

In a further embodiment of this aspect of the invention, the test compound is identified as a potentiator of an inhibitor of cell cycle progression if the ratio of the detectable protein to the total cell number increases in the presence of the compound under conditions where the promoter is activated with little or no change under conditions where the promoter is not activated compared to the total cell number in the absence of the compound.

In another embodiment of this aspect of the invention, the cells, in the absence of a bioactive substance, will proliferate under conditions in which the inducible promoter is not activated. Additionally, the second promoter is activated by the protein that directly or indirectly inhibits cell cycle progression. Thus, the detectable protein will be expressed only at low basal levels under conditions in which the inducible promoter is not activated. If the inducible promoter is activated, the gene in operative association therewith will be transcribed and translated. The resulting protein will inhibit cell cycle progression leading to cell growth arrest and will activate the second promoter and the expression of the detectable protein. The level of cell growth and detectable protein can be measured. The ratio of total content of the detectable protein to the total cell number of cells not treated with a test compound under conditions in which the first promoter is activated or not activated is compared to the ratio of the total content of the detectable protein and the total cell number of cells treated with the test compound under conditions in which the first promoter is activated or not activated In a preferred embodiment of this aspect of the invention, the protein that inhibits cell cycle progression is a cyclin-dependent kinase inhibitor, and in a particularly preferred embodiment this protein is p21. In this embodiment, the test compound is identified as an inhibitor of a downstream effect of the CDK inhibitor on transcription but not of the cell cycle inhibition function of the CDK inhibitor if the ratio of the detectable protein to the total cell number decreases in the presence of the compound under conditions where the promoter is activated, and if there is little or no change in the ratio of the total cell number under conditions where the first promoter is not activated to the total cell number under conditions where the first promoter is activated. Since such compounds do not interfere with the growth-inhibitory activity of the CDK inhibitor, they do not jeopardize the essential role of the CDK inhibitor in cell cycle control but they block the signal transduction pathways that are activated by the CDK inhibitor and that lead to the induction of genes involved in carcinogenesis and different age-related diseases.

In another embodiment of this aspect of the invention, the test compound is identified as inhibitor of the CDK inhibitor protein if the ratio of the total cell number under conditions where the first promoter is not activated to the total cell number under conditions where the first promoter is activated decreases compared to the ratio in the absence of the test compound. Such compounds inhibit the growth-inhibitory effect of the CDK inhibitor and are likely to be direct inhibitors of this protein. The primary use for these compounds may be as chemo- or radio-sensitizing compounds, which may exert their effect by inhibiting CDK inhibitor-mediated checkpoint response and thereby maintaining the cells in a vulnerable cycling condition.

In a third aspect, the invention provides a method for identifying a bioactive substance that has an effect either on cell growth or a promoter responsive to cell cycle inhibition. In the method according to this aspect of the invention, cells comprising a first inducible promoter operatively associated with a gene that encodes a protein that directly or indirectly inhibits cell cycle progression and a second promoter responsive to cell cycle inhibition and operatively associated with a gene encoding a detectable protein are provided and contacted with test bioactive substance under conditions in which the first promoter is activated or not activated. The total cell number and the level of detectable protein are then assayed and the ratio of detectable protein to the total cell number is determined. The test bioactive substance is identified as a substance that has an effect on cell growth if the total cell number under conditions in which the first promoter is activated or not activated is different in the presence of the bioactive substance than in the absence of the bioactive substance. The test bioactive substance is identified as a substance that has an effect on a promoter responsive to cell cycle inhibition if the ratio of detectable protein to the total cell number under conditions in which the first promoter is activated or not activated is different in the presence of the bioactive substance compared to the ratio in the absence of the bioactive substance. All definitions are as described above.

The following examples are intended to further illustrate certain preferred embodiments of the invention and are not intended in any way to limit the invention.

EXAMPLES

Screen

A line of HT 1080 human fibrosarcoma cells with IPTG-inducible p21 (HT1080 p21-9) (Chang et al., Oncogene 18:4808-4818, 1999) was infected with a self-inactivating (SIN) lentiviral vector that expresses GFP from a p21-responsive cytomegalovirus (CMV) promoter. A GFP-positive cell population was isolated by FACS, and individual clonal cell lines were derived from this population. IPTG was added to the cells to induce the expression of p21, and a cell line showing the strongest increase in GFP expression upon the addition of IPTG was selected for screening compounds that modulate the transcriptional effect of p21.

For screening test compounds, cells are plated into two sets of 96-well FluoroNunc plates. The IPTG set receives 2000 cells per well in 100 µl medium containing 100 µM IPTG and the control set receives 1000 cells per well in 100 µl medium without IPTG. Cells are allowed to attach to the plates for 3 hours before 10 µl of each diluted compound is added to the well. After 3 days of culture, the wells are washed once with PBS and cells are lysed for 10 min with 35 µl of cell lysis buffer containing 0.5 µg/ml Hoechst 33342 that stains cellular DNA in proportion to the cell number. A fluorimeter plate reader is used to measure GFP fluorescence at 485 nm for excitation and 520 nm for emission; and Hoechst fluorescence at 355 nm for excitation and 460 nm for emission. Hoechst fluorescence is used as a measure of the cell number and the ratio of GFP to Hoechst fluorescence is used as a measure of normalized promoter activity.

FIG. 1 shows the result of a preliminary assay carried out one day after plating cells in the absence of IPTG, to determine the effect of the number of cells plated in each well on GFP fluorescence (top panel), Hoechst fluorescence (middle panel), and the normalized CMV promoter function, expressed as the ratio of GFP to Hoechst fluorescence (bottom panel). This analysis shows linear correlation between GFP and Hoechst staining with the cell number and the feasibility of carrying out the assay with a wide range of the number of plated cells.

Figure 2:
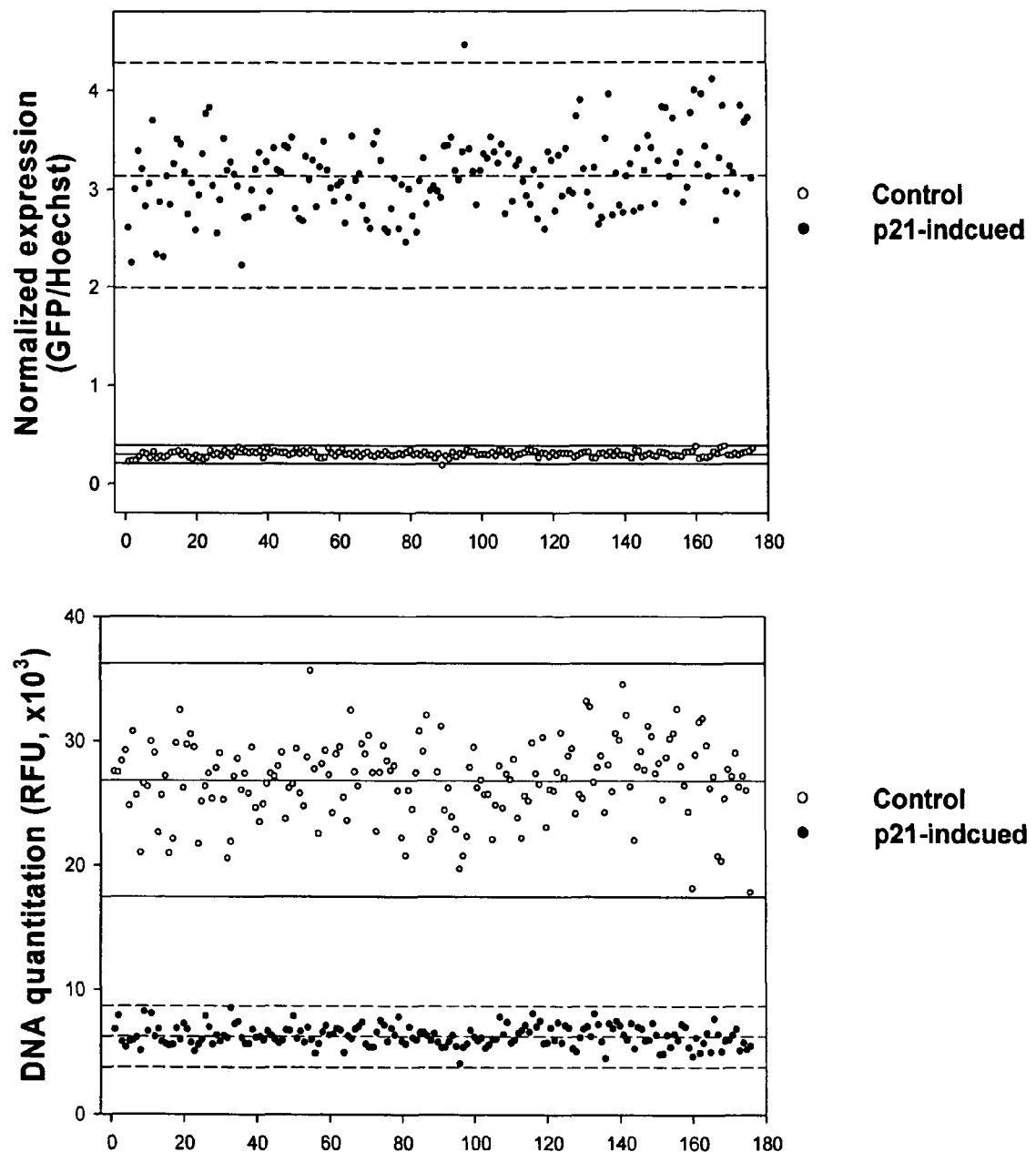
FIG. 2 shows the result of a control complete assay carried out as described in the examples for 88 wells of 96-well plates with and without IPTG, in the absence of any tested compounds.
Figure 3:
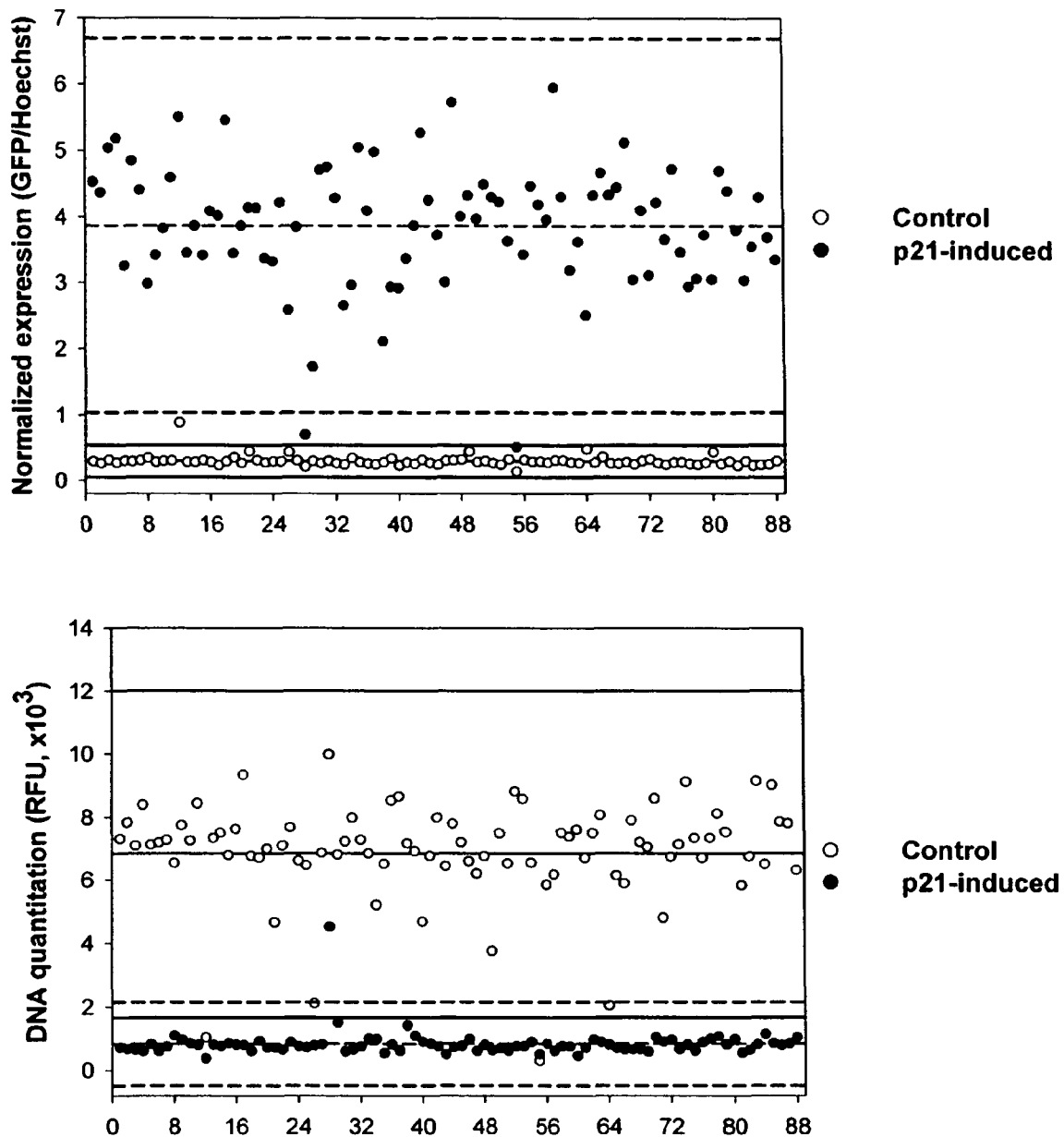
FIG. 3 shows the result of a representative assay for 88 wells of a plate containing 80 compounds from ChemBridge MicroFormat-04 diversified compound collection, tested at 20 µM concentrations.

FIG. 2 shows the result of a control complete assay carried out as described above in two 96-well plates, with 88 wells used in each plate, with and without IPTG, in the absence of any tested compounds. FIG. 3 shows the result of a representative assay for 88 wells of a plate containing 80 compounds from ChemBridge MicroFormat-04 diversified compound collection, tested at 20 µM concentrations. In the top panels of these two figures, each symbol represents the ratio of GFP to Hoechst fluorescence for a single well (normalized expression). In the bottom panels, each symbol represents Hoechst fluorescence for a single well (DNA quantitation). Open symbols are the values for control (IPTG−) plates, and the closed symbols are the values for IPTG+ plates. The horizontal lines represent the means and three standard deviations for the IPTG+ and IPTG− cells, respectively.

This analysis shows the range of variability for the assay. The GFP/Hoechst ratios of control (untreated) cells show very tight clustering, indicating the reproducibility of cell plating, growth and basal CMV promoter activity, despite the relatively long (3-day) duration of culture. The GFP/Hoechst ratios of the IPTG-untreated cells show greater variation, reflecting variability in the promoter induction, but all the values for IPTG-treated cells are much higher than the values for the untreated cells.

The values for tested compounds falling outside the range may be considered as tentative hits. The confirmation rate for such hits identified should vary depending on the stringency of the criteria used to select the specific class of compounds. For example, screening 5,120 ChemBridge compounds yielded 61 tentative hits for compounds that decrease normalized GFP expression in IPTG-treated wells by an arbitrarily chosen value of ≥2.5-fold (1.2% hit rate). 60 of these compounds were picked and re-tested, and 20 of them were confirmed for this activity (33.3% confirmation rate).

Subsequent testing of the confirmed hits is required to rule out obvious artifacts that may result from the nature of the assay. For example, a potential artifact in the use of Hoechst 33342 is that a tested compound may fluoresce in the same range as this dye (355 excitation/420 emission). The 20 confirmed hits therefore were tested for fluorescence in the above range, and 10 of them were shown to produce fluorescence overlapping with that of the Hoechst dye. Of the remaining 10 compounds, 8 decreased the cell number of IPTG+ cells, suggesting considerable toxicity, but the other two compounds decreased promoter induction by p21 without significant toxicity to p21-induced cells. Such compounds can therefore be considered as potentially promising p21 pathway inhibitors.

This assay was used to screen two diversified compound libraries from ChemBridge Corp., DiverSet and MicroFormat 04, each comprising 50,000 compounds. A total of 62 compounds of 100,000 were identified and verified as decreasing normalized GFP expression in IPTG-treated wells, i.e. as inhibitors of cell cycle arrest-activated transcription. A total of 788 compounds were identified and verified as decreasing the proliferating cells (in IPTG− wells), and 223 of the latter strongly [>2.5-fold] decreased cell number in IPTG+ wells, i.e. were toxic to growth-arrested cells. Of the remaining growth-inhibitory compounds, 216 showed preferential inhibition of cell number in the IPTG− wells relative to IPTG+ wells, i.e. were identified as growth inhibitory compounds with specificity for proliferating cells.

We claim:

1. A method for identifying a small molecule test compound that inhibits a promoter activated by cell cycle inhibition comprising: (a) providing cells comprising a first inducible promoter linked to a gene that encodes a protein that directly or indirectly inhibits cell cycle progression and a recombinant expression vector comprising a reporter gene encoding a detectable protein under transcriptional control of a second promoter that is activated by cell cycle inhibition; (b) dividing the cells into four aliquots; (c) treating the first aliquot with a small molecule test compound, wherein said first promoter is activated; (d) treating the second aliquot with the small molecule test compound, wherein said first promoter is not activated; (e) providing the third aliquot, wherein the third aliquot is not treated with the small molecule test compound and wherein said first promoter is activated; (f) providing the fourth aliquot, wherein the fourth aliquot is not treated with the small molecule test compound and wherein said first promoter is not activated; (g) determining total cell number of each aliquot; (h) determining the amount of the detectable protein in each aliquot; (i) calculating the ratio of detectable protein to the total cell number for each aliquot; and (j) comparing the ratio of each aliquot, wherein the small molecule test compound is identified as a small molecule compound that inhibits a promoter activated by cell cycle inhibition if the ratio from the third aliquot is higher than the ratio of the first aliquot, which is higher than the ratio from the fourth aliquot, which is equal to or higher than the ratio from the second aliquot.

2. The method of claim 1, wherein the second promoter is activated by the protein that directly or indirectly inhibits cell cycle progression.

3. The method according to claim 2, wherein the protein expressed from the first promoter is p21.

4. The method according to claim 1, wherein the total cell number is determined by assaying the total DNA content of each aliquot of the cells.

5. The method according to claim 4, wherein total DNA content of the cells is assayed by adding a detectable DNA binding agent and measuring the amount of the detectable DNA binding agent associated with DNA.

6. The method according to claim 5, wherein the DNA binding agent is detected by fluorometry.

7. The method according to claim 6, wherein the DNA binding agent is Hoechst 33342.

8. The method according to claim 1, wherein the detectable protein is a fluorescent protein.

9. The method according to claim 8, wherein the fluorescent protein is detected by fluorometry.

10. The method according to claim 9, wherein the fluorescent protein is green fluorescent protein.

* * * * *